United States Patent
Spahn (10) Patent No.: US 9,417,339 B2
(45) Date of Patent: *Aug. 16, 2016

(54) COUNTING DIGITAL X-RAY DETECTOR AND METHOD FOR TAKING A SERIES OF X-RAY IMAGES

(71) Applicant: Siemens Aktiengesellschaft, Munich (DE)

(72) Inventor: Martin Spahn, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 251 days.

This patent is subject to a terminal disclaimer.

(21) Appl. No.: 13/939,925

(22) Filed: Jul. 11, 2013

(65) Prior Publication Data

US 2014/0016748 A1 Jan. 16, 2014

(30) Foreign Application Priority Data

Jul. 11, 2012 (DE) .......................... 10 2012 212 124

(51) Int. Cl.
*H01L 27/148* (2006.01)
*G01T 1/24* (2006.01)
(Continued)

(52) U.S. Cl.
CPC ............... *G01T 1/247* (2013.01); *A61B 6/4241* (2013.01); *G01T 1/245* (2013.01); *G01T 1/246* (2013.01);
(Continued)

(58) Field of Classification Search
CPC ...... A61B 6/42; A61B 6/4208; A61B 6/4233; A61B 6/4241; A61B 6/52; A61B 6/5205; H01L 27/146; H01L 27/14676; H01L 27/148; H01L 27/14806; G01T 1/16; G01T 1/17; G01T 1/20; G01T 1/2006; G01T 1/2018; G01T 1/208; G01T 1/24; G01T 1/245; G01T 1/246; G01T 1/247; H04N 5/372; H04N 5/37206; H04N 5/37213; H04N 5/3745; H04N 5/37452; H04N 5/378; G11C 19/00; H03K 21/00; H03K 21/08; H03K 21/12; H03K 21/14; H03K 21/38; H03K 23/002

USPC .............. 378/19, 91, 98, 98.8, 114, 204, 210, 378/901; 250/271, 370.01, 370.08, 370.09, 250/370.11, 371, 395, 526; 711/5, 100, 711/109, 117, 154, 159, 166; 377/1, 37, 64, 377/76, 107, 118, 130

See application file for complete search history.

(56) References Cited

U.S. PATENT DOCUMENTS

| | | | |
|---|---|---|---|
| 6,248,990 B1 | 6/2001 | Pyyhtia et al. | 250/208.1 |
| 7,332,724 B2 | 2/2008 | Hefetz et al. | 250/370.06 |

(Continued)

FOREIGN PATENT DOCUMENTS

| | | | |
|---|---|---|---|
| DE | 69711902 T2 | 11/2002 | G01T 1/24 |
| DE | 102005060310 A1 | 6/2007 | G01T 1/29 |
| DE | 112006001859 T5 | 5/2008 | G01N 23/04 |

OTHER PUBLICATIONS

Spahn, Martin, "Flat Detectors and Their Clinical Applications," Eur Radiol, vol. 15, 14 pages, Mar. 1, 2005.

*Primary Examiner* — Anastasia Midkiff
(74) *Attorney, Agent, or Firm* — Slayden Grubert Beard PLLC (57) ABSTRACT

A counting digital X-ray detector for taking X-ray images of an object penetrated by X-ray radiation may include at least one detector module having an X-ray converter for converting X-ray radiation into an electrical signal and a matrix having a large number of counting pixel elements, wherein each counting pixel element has a signal input, a conversion device for converting the electrical signal into a count signal and a first digital storage unit for storing the count signal, wherein exactly one second digital storage unit is allocated to each first storage unit, and this is designed to form a copy of the first storage unit at the moment of transfer by way of a transfer process, and wherein the X-ray detector is designed in such a way that the transfer process can be carried out simultaneously for the large number of pixel elements.

18 Claims, 11 Drawing Sheets

(51) Int. Cl.
  *A61B 6/00*    (2006.01)
  *H04N 5/372*   (2011.01)
  *H04N 5/3745*  (2011.01)
  *G01N 23/04*   (2006.01)
  *G01T 1/17*    (2006.01)
  *H04N 5/32*    (2006.01)

(52) U.S. Cl.
  CPC .......... *H04N 5/37452* (2013.01); *A61B 6/4441* (2013.01); *G01N 23/04* (2013.01); *G01T 1/17* (2013.01); *H01L 27/14806* (2013.01); *H04N 5/32* (2013.01); *H04N 5/3745* (2013.01); *H04N 5/37213* (2013.01)

(56) References Cited

U.S. PATENT DOCUMENTS

| | | | |
|---|---|---|---|
| 7,470,910 B2 | 12/2008 | Spahn | 350/370.09 |
| 2007/0005278 A1* | 1/2007 | Brunnett | 702/78 |
| 2009/0290680 A1 | 11/2009 | Tumer et al. | 378/62 |
| 2009/0302232 A1* | 12/2009 | Grosholz et al. | 250/394 |
| 2011/0210235 A1* | 9/2011 | Dierickx | 250/214 R |
| 2013/0228693 A1* | 9/2013 | Soh et al. | 250/370.09 |
| 2013/0341521 A1* | 12/2013 | Fechner | 250/370.14 |

* cited by examiner

COUNTING DIGITAL X-RAY DETECTOR AND METHOD FOR TAKING A SERIES OF X-RAY IMAGES

CROSS-REFERENCE TO RELATED APPLICATIONS

This application claims priority to DE Patent Application No. 10 2012 212 124.2 filed Jul. 11, 2012. The contents of which is incorporated herein by reference in its entirety.

TECHNICAL FIELD

This disclosure relates to a counting digital X-ray detector and to a method for taking a series of X-ray images.

BACKGROUND

Figure 2:
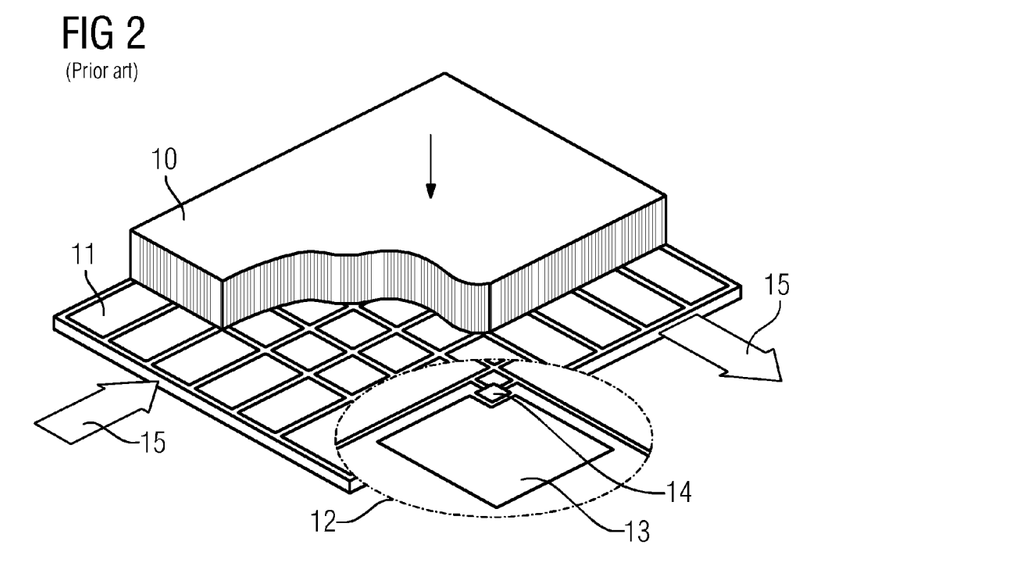
FIG. 2 shows a view of a known X-ray detector with a scintillator.

X-ray systems are used for imaging for diagnostic examination and for interventional procedures, for example in cardiology, radiology and surgery. X-ray systems 16, as shown in FIG. 2, have an X-ray tube 18 and an X-ray detector 17, jointly arranged for example on a C-arm 19, a high voltage generator for generating the tube voltage, an imaging system 21 (often including at least one monitor 22), a system control unit 20 and a patient couch 23. Systems having two planes (2 C-arms) are also used in interventional radiology. Flat panel X-ray detectors are generally used as X-ray detectors in many fields of medical X-ray diagnostics and intervention, by way of example in radiography, interventional radiology, cardio-angiography, but also the treatment for imaging within the framework of control and irradiation treatment planning or mammography.

Figure 1:
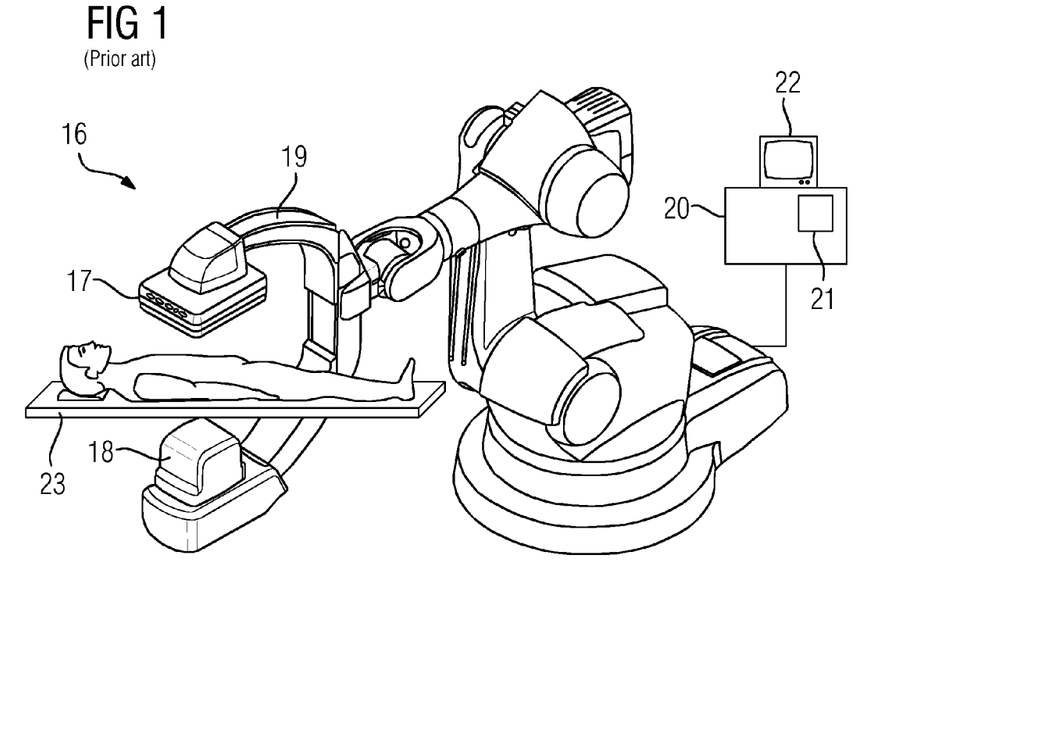
FIG. 1 shows a view of a known X-ray system for use in interventional procedures.

Current flat panel X-ray detectors are generally integrating detectors and are predominantly based on scintillators whose light is converted into electrical charge in matrices of photodiodes. These are then read conventionally line-by-line by way of active control elements. FIG. 1 shows the principle construction of a currently used indirectly-converting flat panel X-ray detector, having a scintillator 10, an active reading matrix 11 made of amorphous silicon having a large number of pixels 12 (with photodiode 13 and switching element 14) and electronic control and reading device 15 (see for example M. Spahn, "Flat detectors and their clinical applications", Eur Radiol. (2005), 15: 1934-1947). Depending on the radiation quality, the quantum efficiency for a scintillator made of CsJ with a layer thickness of for example 600 µm, depending on radiation quality, lies between about 50% and 80% (see for example M. Spahn, "Flat detectors and their clinical applications", Eur Radiol (2005), 15: 1934-1947). The spatial frequency-dependent DQE(f) ("detective quantum efficiency") is upwardly limited hereby and for typical pixel sizes of for example 150 m to 200 µm and for the spatial frequencies of interest to the applications of 1 to 2 lp/mm much lower. To enable new applications (for example Dual-Energy, Material-Separation), but to also further increase quantum efficiency, the potential of counting detectors or energy-discriminating counting detectors primarily based on directly-converting materials, such as CdTe or CdZTe (CZT) and contacted ASICs (application specific integrated circuit; for example embodiment in CMOS technology), is increasingly being examined.

Figure 3:
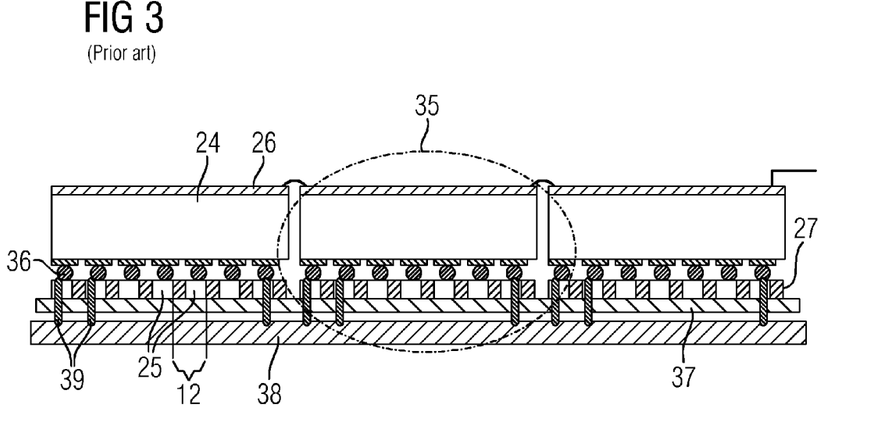
FIG. 3 shows a plan view of a detail of a known X-ray detector with a plurality of detector modules.

FIG. 3 shows the basic construction of such counting detectors. X-ray radiation is converted in a direct converter 24 (for example CdTe or CZT) and the generated charge carrier pairs separated by an electrical field, which is generated by a shared top electrode 26 and a pixel electrode 25. In one of the pixel-like pixel electrodes 25 of the ASIC 27 the charge generates a charge pulse, the size of which corresponds to the energy of the X-ray quantum and which, if above a defined threshold value, is registered as a count event. The threshold value is used to distinguish an actual event from electronic noise or for example to also suppress k-fluorescence photons, in order to distinguish multiple counts. The ASIC 27, a corresponding section of the direct converter 24 and a coupling between direct converter 24 and ASIC 27 (in the case of directly-converting detectors for example by means of bump bonds 36) each form the detector module 35 having a large number of pixel elements 12. The ASIC 27 is arranged on a substrate 37 and connected to peripheral electronic devices 38. A detector module can also have one of more ASIC(s) and one or more parts of a direct converter, chosen as required in each case.

Figure 4:
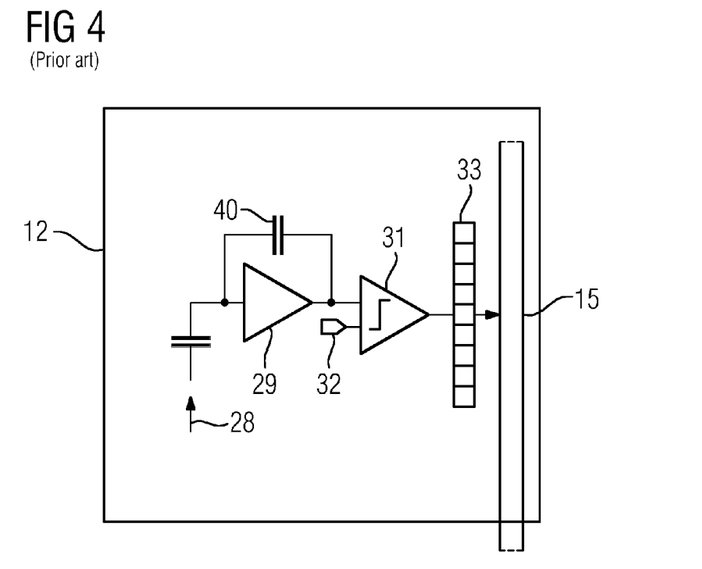
FIG. 4 shows a diagram of the central functional elements of a counting pixel element of a known X-ray detector.
Figure 5:
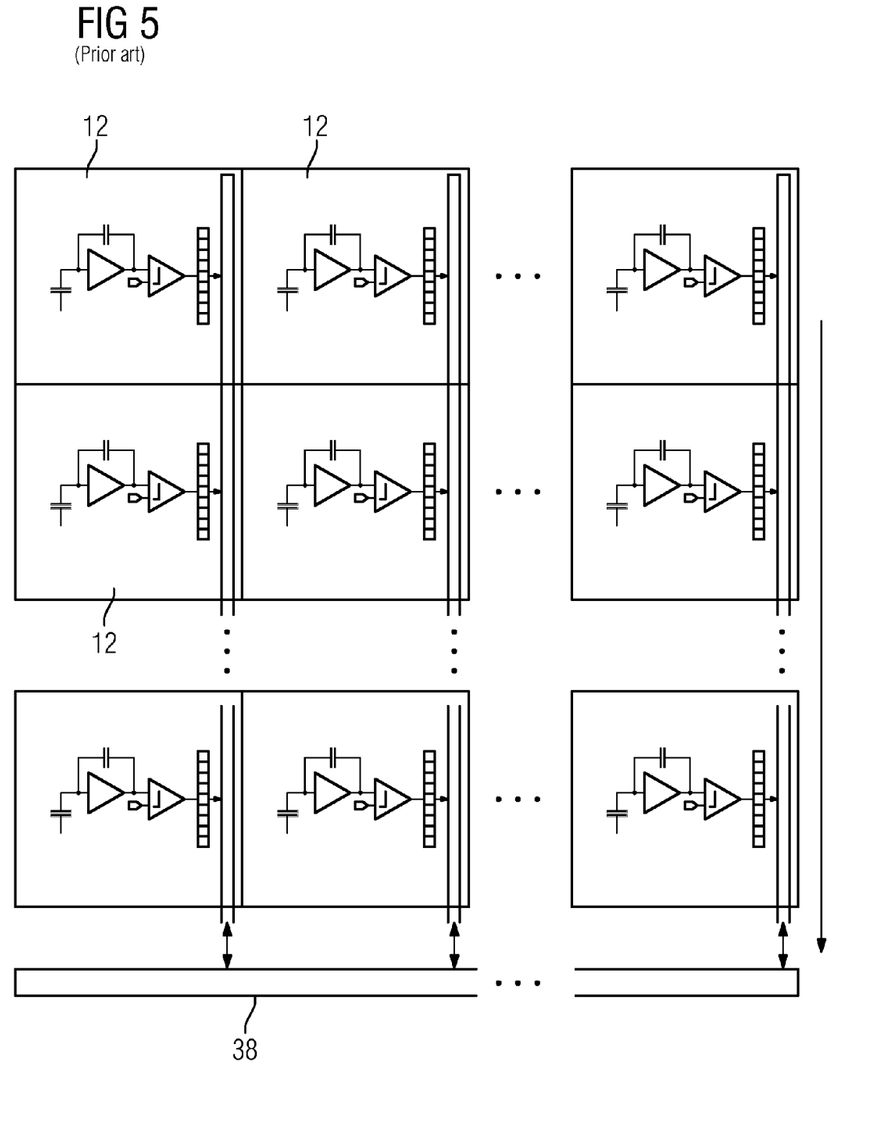
FIG. 5 shows a diagram of a matrix comprising counting pixel elements of a known X-ray detector with control and reading logic.

FIG. 4 shows the general diagram of a counting pixel element. The electrical charge passes the charge input 28, is collected in the pixel element and amplified there with the aid of a charge amplifier 29 and a feedback capacitor 40. The pulse shape can also be adjusted at the output in a shaper (filter) (not shown). An event is then counted in that a digital storage unit (counter) 33 is incremented by one if the output signal lies above an adjustable threshold value. This is established by way of a discriminator 31. The threshold value can in principle also be predetermined in a strictly analogue manner, but in general is applied across for example a DAC 32 (digital to analog converter) and can be variably adjusted in a certain region thereby. A reading can then be made by way of a control and reading unit 34. FIG. 5 shows a corresponding diagram for an entire array of counting pixel elements 12, for example 100×100 pixel elements each of, for example, 180 µm. Such an array is implemented with the aid of the ASIC. In this example it has a size of $1.8 \times 1.8$ cm$^2$. For large-area detectors (for example $20 \times 30$ cm$^2$) a plurality of detector modules 35 is combined (in this example 11×17 would produce roughly this area) and is connected by the shared peripheral electronic devices. TSV technology (through silicon via) for example is used for the connection between ASIC and peripheral electronic devices.

In the case of counting and energy-discriminating X-ray detectors two, three or more threshold values are introduced and the size of the charge pulse, corresponding to the predefined threshold values (discriminator thresholds), are classified in one or more of the digital storage unit(s) (counters). The X-ray quanta counted in a certain energy field may then be obtained by calculating the difference in the counter contents of two corresponding counters. The discriminators may be adjusted for example with the aid of DACs (digital-to-analog converter) for the whole detector module or pixel-by-pixel within given limits or ranges. The counter contents of the pixel elements are successively read module-by-module by a corresponding reading unit. This reading process requires a certain amount of time during which counting cannot continue without errors.

In a pulsed radiation mode of the X-ray system an X-ray radiation window and a reading window must be defined as in the case of integrating detectors. With an image frequency of for example 50 fps (frames per second; frame time for example 20 ms) and a reading time of 10 ms an X-ray window for a maximum pulse width of 10 ms remains (frame time=radiation time plus reading time). In this example (for example 10,000 pixels per detector module) a single pixel element is read at 1 µs (10,000×1 µs=10 ms). A design of this kind, which as in this example requires 1 µs reading time per pixel element, already reaches its limits at an image rate of 100 fps since the X-ray window then shrinks to 0 ms.

In the case of continuous radiation, the radiation process continues during the reading process and can consequently either not be counted (no use of the radiation dose) or, if this is not ruled out by the design, the count signals each correspond to slightly different periods of time, and this is something which should be avoided at all costs. Higher switching frequencies of for example 10 MHz can lower the reading time for the example detector module to 1 ms, but at 100 fps there is still a ratio of 1:9 between reading time and usable radiation time.

SUMMARY

One embodiment provides a counting digital X-ray detector for taking X-ray images of an object penetrated by X-ray radiation, having at least one detector module, the detector module having an X-ray converter for converting X-ray radiation into an electrical signal and a matrix having a large number of counting pixel elements, wherein each counting pixel element has a signal input, a conversion device for converting the electrical signal into a count signal and a first digital storage unit for storing the count signal, wherein exactly one second digital storage unit is allocated to each first storage unit and is designed to form a copy of the first storage unit at the moment of transfer by way of a transfer process, and wherein the X-ray detector is designed in such a way that the transfer process can be carried out simultaneously for the large number of pixel elements.

In a further embodiment, the conversion device has a charge amplifier and at least one discriminator each with an adjustable threshold value.

In a further embodiment, the conversion device has a plurality of discriminators each with different threshold values and the pixel element has a plurality of first digital storage units for counting count signals of different levels.

In a further embodiment, the X-ray converter is formed by a direct converter, in particular CdTe.

In a further embodiment, the X-ray detector has a large number of detector modules.

In a further embodiment, the digital storage units are formed by counters.

Another embodiment provides a method for taking a series of X-ray images of an object with a counting digital X-ray detector as disclosed above, wherein (a) X-ray radiation penetrating the object during an X-ray window is converted in a spatially resolved manner into electrical signals, (b) the electrical signals are converted pixel-by-pixel into count signals and are stored in the respective first storage units, (c) the stored count signals of all pixel elements are simultaneously transferred from the first storage units into the second storage units and then the first storage units are re-set to zero, (d) the contents of the second storage units are then sequentially read from the X-ray detector and the second storage units are re-set to zero, and (e) the steps are repeated several times in the sequence a to d, wherein steps a and b occur at least partially while step d of the preceding sequence is being carried out.

BRIEF DESCRIPTION OF THE DRAWINGS

Aspects of the invention and example embodiments are discussed herein with references to the drawings, in which.

DETAILED DESCRIPTION

Embodiments of the present invention provide a counting digital X-ray detector which enables high frame rates with high image quality of X-ray images for interventional applications. Other embodiments provide a corresponding method for taking a series of X-ray images.

One embodiment provides a counting digital X-ray detector for taking X-ray images of an object penetrated by X-ray radiation, having at least one detector module, comprising an X-ray converter for converting X-ray radiation into an electrical signal and a matrix comprising a large number of counting pixel elements, wherein each counting pixel element has a signal input, a conversion device for converting the electrical signal into a count signal and a first digital storage unit for storing the count signal, wherein exactly one second digital storage unit is allocated to each first storage unit, and this is designed to form a copy of the first storage unit at the moment of transfer by way of a transfer process, is designed in such a way that the transfer process is simultaneously carried out for the large number of pixel elements.

With the disclosed X-ray detector the count contents of the first digital storage units can be transferred to the second digital storage units ("shadow storage devices") within a very short time and for all pixel elements simultaneously, so the first storage units can be re-set to zero very quickly and are thereby free for new counting operations. The reading process, which generally occurs sequentially and requires a relatively long time, can consequently be shifted to the second digital storage units. In this way new X-ray radiation can again be evaluated very quickly and yet at the same time as the reading process and count signals can be stored in the first digital storage unit. The frame rate when taking series of X-ray images can thus be significantly increased and a high image quality retained in the process.

The first digital storage unit can in particular be a counter with the task of both incrementing a count event with each electrical signal, which lies above a corresponding discriminator threshold value, and of storing the corresponding counter content. A digital register, shift register or sequential logic system for example can be used as a counter, and this is incremented by a count unit as soon as there is a logic pulse (here from the discriminator) at its input. The register is set to zero at the start of a count period. The counter can be read sequentially or simultaneously. The second digital storage unit can be a pure storage device which is capable of receiving and buffering a copy of the counter reading of the first digital storage unit. This storage device can also be a register which can be written on or read either sequentially or simultaneously.

Another embodiment provides a method for taking a series of X-ray images is as follows:
a) X-ray radiation penetrating the object during an X-ray window is converted in a spatially resolved manner into electrical signals,
b) the electrical signals are converted pixel-by-pixel into count signals and are stored in the respective first storage units,
c) the stored count signals of all pixel elements are simultaneously transferred from the first storage units into the second storage units and then the first storage units are re-set to zero,
d) the contents of the second storage units are then sequentially read from the X-ray detector and the second storage units are re-set to zero, and
e) the steps are repeated several times in the sequence a to d, wherein steps a and b occur at least partially while step d of the preceding sequence is being carried out.

According to one embodiment the conversion device has a charge amplifier and at least one discriminator each with an adjustable threshold value. The threshold value can be applied for example across a DAC. In this way only electrical signals which exceed the threshold value are counted, so noise can be faded out or only events with energies above a desired threshold are counted. Window discriminators can also be provided which have both a lower and an upper threshold value, so only events whose energy is above the lower threshold value and below the upper threshold value are counted in the corresponding counter. The upper threshold value can therefore be set for example such that it is not higher than the maximum expected X-ray energy.

According to a further embodiment the conversion unit has a plurality of discriminators each with different threshold values and the pixel element has a plurality of first digital storage units for counting count signals of different levels. Each electrical signal is consequently classified in the corresponding first storage unit according to its signal level. In this way energy-selective imaging is possible since the level of the electrical signal is determined by the energy of the X-ray quantum by way of which it was generated. Two, three, four or a large number of first storage units and threshold values may be provided. A corresponding number of second digital storage units is of course likewise provided.

According to a further embodiment the X-ray converter is formed by a direct converter, in particular CdTe (cadmium telluride). Other direct converter materials such as CZT (cadmium zinc telluride), HgI, PbO, etc. may also be used. Direct converters of this kind have the advantage of generating high electrical signals and count rates since the layer thicknesses may be much higher than for example in the case of indirect converters, so there is higher absorption. As a result, higher DQEs (Detective Quantum Efficiency) are in turn possible over the entire spatial frequency range.

The X-ray detector advantageously has a large number of detector modules. Large-area X-ray detectors may thus be produced.

The (first and second) digital storage units are expediently formed by counters.

Figure 6:
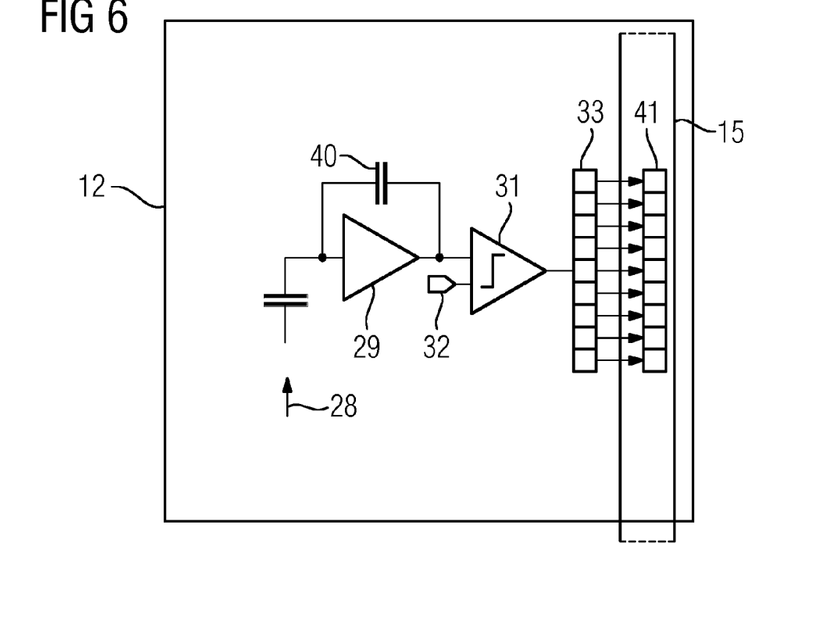
FIG. 6 shows a diagram of the central functional elements of a counting pixel element of an X-ray detector with a first and a second digital storage element, according to one embodiment of the invention.

FIG. 6 shows the central functional elements of a pixel element of a digital counting X-ray detector, according to one embodiment of the invention. Apart from the charge input 28, charge amplifier 29, feedback capacitor 40, discriminator 31, DAC 32 and first digital storage unit 33 a second digital storage unit 41 ("shadow storage device") is arranged in the pixel element. By way of a transfer process the content of the first digital storage unit is very quickly transferred into the second digital storage unit and a 1:1 copy of the first storage unit is generated in the second storage unit 41. This may be easily carried out such that this transfer process occurs simultaneously for all pixel elements of a detector module or the entire X-ray detector. Depending on the architecture of the storage units this can be carried out successively bit for bit for each storage unit or for all bits simultaneously. In the case of a clock frequency of 1 MHz (it is assumed here that one bit or—in the case of parallel architecture—all bits of the counter are transferred simultaneously within a clock. If a plurality of clocks are required per bit transfer, this is of course multiplied accordingly) this transfer process can be carried out within one or a few µs, in the case of 10 MHz even within 100 ns or a few 100 ns. Such times are negligibly low for image frequencies of for example 100-500 fps or corresponding time windows of 10 ms-2 ms—for both pulsed and continuous X-ray radiation. The contents of the first storage units are then reset to zero and the count signals can be read from the second storage unit by means of the electronic control and reading device 34.

Reading from the second storage units then occurs within the time window corresponding to the image frequencies (called counting intervals below) to enable the next transfer from the first storage unit to the second storage unit. In an example of 10,000 pixel elements this lasts 10 ms or 1 ms accordingly with a clock frequency of 1 MHz or 10 MHz (by way of simplification it is assumed that the transfer of an entire count content is possible within a clock cycle, i.e. all bits of a counter are read simultaneously; if this occurs sequentially, the time then increases in accordance with the bit depth of the counters and reduces the possible image frequencies accordingly). For a clock frequency of 1 MHz image rates of up to 100 fps and for 10 MHz image rates of up to 1,000 fps may therefore be achieved.

Figure 7:
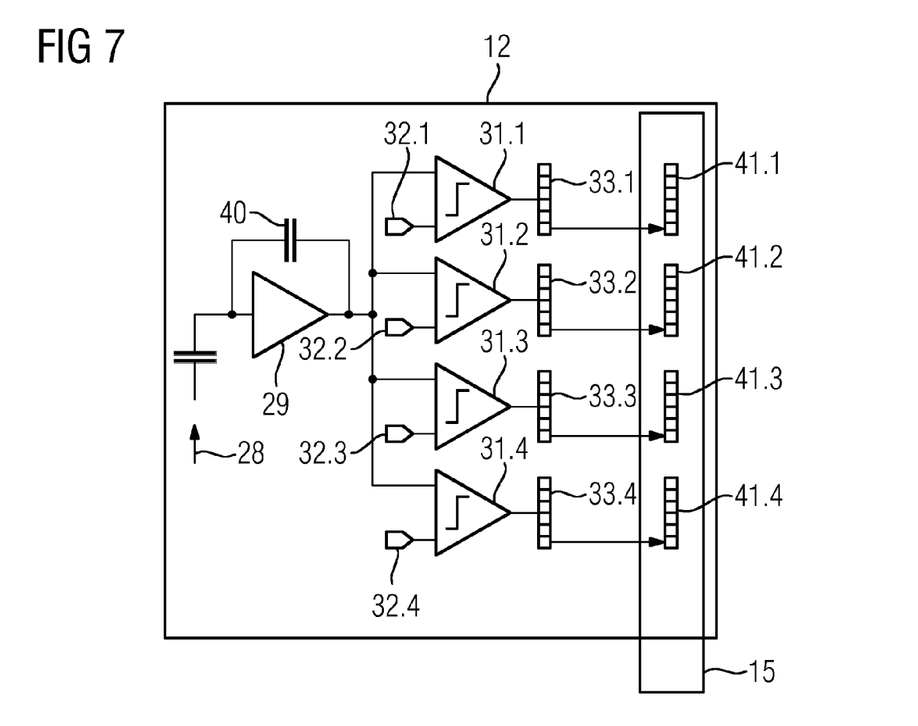
FIG. 7 shows a diagram of the central functional elements of a counting, energy-discriminating pixel element of an X-ray detector having a plurality of first and second digital storage elements, according to one embodiment of the invention.

FIG. 7 shows a further example for the central functional elements of a pixel element of a digital counting X-ray detectors, according to one embodiment of the invention. In this example the pixel element 12 has a plurality of, for example four, first digital storage units 33.1, 33.2, 33.3, 33.4 each with a DAC 32.1, 32.2, 32.3, 32.4 with different threshold values. Energy-selective imaging can be carried out with a construction of this kind. One second digital storage unit 41.1, 41.2, 41.3, 41.4 respectively is allocated to each first digital storage unit 33.1, 33.2, 33.3, 33.4, i.e. arranged in the pixel element for example. The contents of all first storage units can be simultaneously transferred as 1:1 copies to the second storage units for all pixel elements by way of a transfer process in this case as well. The first storage units can then be reset to zero and then be used further (written on) while the contents are being read from the second storage units.

Figure 8:
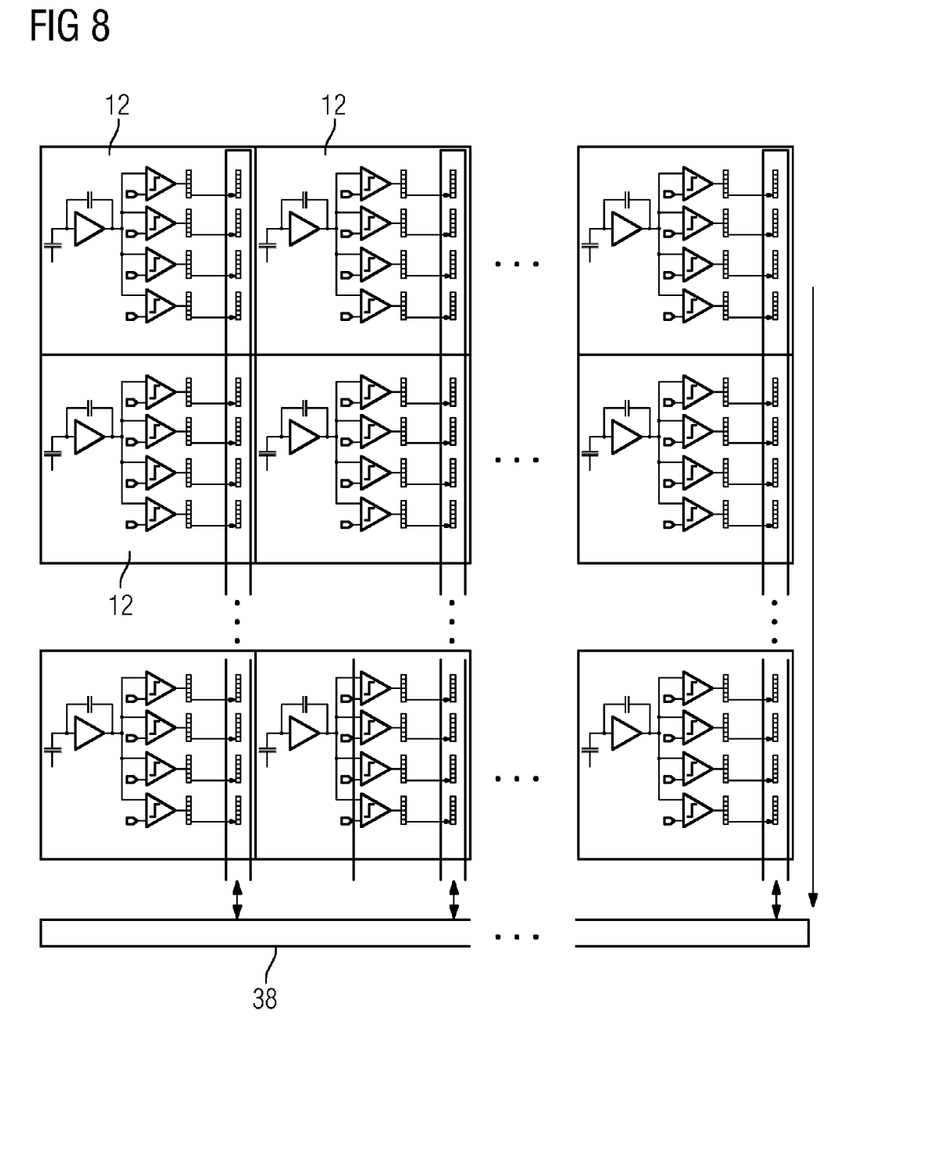
FIG. 8 shows a diagram of a matrix comprising counting pixel elements according to FIG. 7 of an X-ray detector, according to one embodiment of the invention.

FIG. 8 shows a corresponding schematic diagram for an ASIC with counting pixel elements 12 as shown in FIG. 7, for example 100×100 pixel elements. In the standard case a detector module has one ASIC and a continuous piece of a direct converter. However, it may also be provided that a detector module has a plurality of ASICs and/or a plurality of parts of a direct converter.

Figure 14:
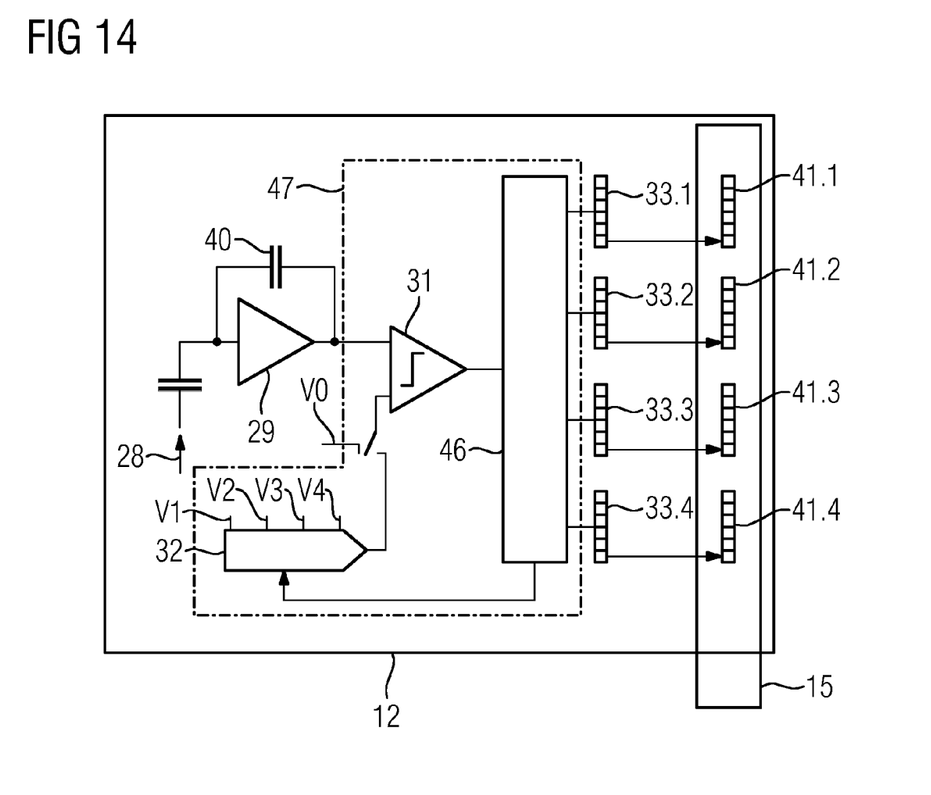
FIG. 14 shows a diagram of the central functional elements of a counting, energy-discriminating pixel element having a discriminator with a plurality of threshold values.

FIG. 14 shows a further example of the central functional elements of a pixel element, operating energy-selectively, of a digital counting X-ray detector, according to one embodiment of the invention. Instead of four separate discriminators as in FIG. 7 the pixel element has one ADC (analog digital converter) 47 with successive approximation, i.e. with one discriminator 31 and one DAC 32, wherein the DAC 32 successively generates the increasing threshold values V1 to V4 and successively applies them at the discriminator. The corresponding first digital storage element (1 to 4) is increased by one bit if the detector signal lies above the threshold value (1 to 4). The successive approximation logic 46 then ensures that the next higher threshold value is generated at the DAC 32, and this is then again applied at the comparator. The ADC is started by moving a switch as soon as there is a signal at the discriminator which is higher than a start threshold value V0, which, in turn, must be lower than the first threshold value V1. One second digital storage unit 41.1, 41.2, 41.3, 41.4 respectively is allocated to each first digital storage unit 33.1, 33.2, 33.3, 33.4. The contents of all first storage units can be simultaneously transferred as 1:1 copies to the second storage units for all pixel elements by way of a transfer process in this case as well.

The digital storage units can be formed by what are known as counters.

The counter depth (number of bits) depends on both the maximum expected count rate and the count time during which count signals are registered. If the count time, during which count signals accrue (hereinafter called "counting interval"), and the X-ray window can be fixed independently of each other, then additional degrees of freedom are obtained. Important free parameters are the transfer time (time for simultaneously (parallel) transferring the contents of the first storage units for all pixel elements into the second storage units), the (detector) module reading time, the X-ray window length (the time within which radiation is to be detected for a resulting X-ray image irrespective of whether pulsed or continuous radiation is applied) and the counting interval.

Some examples are given by way of clarification below:

1. The maximum count rate is for example 100 Mcps/mm$^2$ (Mcps=Mega counts per second), i.e. with a pixel size of 180*180 μm$^2$ about 3 Mcps per pixel element. The pixel matrix per detector module is for example 100×100 pixel elements. The in-pixel transfer time (transfer of the contents of the first storage units into the corresponding second storage units) is for example 100 ns, the transfer time of the pixel content(s) out of the pixel element into the detector periphery (module reading time) is also 100 ns. In the case of sequential transfer the total transfer time of the contents of the second counter(s) into the detector periphery for the module is then 10,000×100 ns=1 ms. The X-ray window length is for example a minimum of 10 ms. With a counting interval of 1 ms (10× readings during the X-ray window length—the count interval must be at least as long as the module reading time) the maximum expected count rate is 3,000 cps (3 Mcps*1 ms=3,000 cps), from which a required bit depth of 12 bits follows. With a counting interval of 10 ms (i.e. as long as the X-ray window) the max. expected count rate is 30,000, so a counter bit depth of 15 bits is required.

2. For another application the maximum count rate is for example 500 Mcps/mm$^2$ and the pixel size 300*300 μm$^2$. This corresponds therefore to about 45 Mcps per pixel element. The pixel matrix per detector module is for example 71*71 pixel elements (5,041 pixel elements per detector module). The in-pixel transfer time is for example about 20 ns (assumption: about 50 MHz clock rate and transfer of the content of the first storage units into the corresponding second storage units within a clock cycle), the module reading time is for example 100 μs (about 20 ns×5,041 produces about 100 μs; assumption: all bits of the second storage unit of a pixel element are read simultaneously and within a clock cycle into the peripheral electronic devices) and the X-ray window length is for example a minimum of 2 ms. The counting interval, which must be longer than the module reading time, is for example 200 μs (i.e. during the X-ray window the first storage unit is reset 10 times or transferred into the corresponding second storage unit). The maximum expected count rate is then 45 Mcps*200 μs=9000 and a bit depth of 14 bits is sufficient.

With a counting interval of 1 ms (2× readings during the X-ray window length) the maximum expected count rate is 45,000, from which a required bit depth of 16 bits follows.

3. For a third application the maximum count rate is for example 50 Mcps/mm$^2$. With a pixel size of 180*180 μm$^2$ these are slightly more than 1.6 Mcps per pixel element. The pixel matrix per detector module is for example 100×100 pixel elements. The in-pixel transfer time is for example 20 ns (assumption: 50 MHz clock rate and transfer of the content of the first storage units into the corresponding second storage units within a switching cycle), the module reading time 200 μs (assumption all bits of a second storage unit are read simultaneously and within a clock cycle into the detector periphery; 10,000 pixels×20 ns=200 μs), the X-ray window length is a minimum of 2 ms. With a counting interval of 200 μs (10× readings during the X-ray window length—the counting interval must be at least as long as the module reading time) the maximum expected count rate is 300, from which a required bit depth of 9 bits follows. With a counting interval of 2 ms (as long as the X-ray window therefore) the maximum expected count rate is 3,000, so a counter bit depth of 12 bits is required.

Overall it is advantageous to orient the design such that the counting interval is always at least as long as the module reading time, the module reading time is at most as long as the shortest X-ray window, the counter bit depth is deep enough to cover the highest count rates per pixel element and counting interval and the transfer time from the first storage unit into the second storage unit and the resetting time of the first storage unit are negligible with respect to a counting interval (for example 1% thereof or less).

In the three examples it has been assumed that the content of the first storage unit is transferred into the second storage unit within a switching interval (data transfer within the pixel element) or the content of the second storage unit of each pixel element is also transferred to the peripheral electronic devices of the X-ray detectors when the detector module is read. If the bit contents are transferred sequentially instead of simultaneously for example, the respective transfer takes longer accordingly (i.e. with an 8 bit counter, 8 times as long for example). Depending on the definition or implementation a plurality of switching intervals could also be necessary to carry out certain ASIC operations such as the transfer of bit contents from one storage device into another. The transfer or reading times are then correspondingly longer. The examples should, however, only be used to highlight the general dependencies of the various design definitions on each other and on the application boundary conditions.

In the case of a plurality of first and accordingly second storage units per pixel element—depending on the design—the second storage units may also be read simultaneously or sequentially. The following cases are conceivable: (1) completely simultaneously: all bits of all first storage devices of a pixel element are simultaneously transferred into the corresponding bits of the second storage devices of the pixel element, (2) semi-simultaneously: simultaneously for all first storage devices of a pixel element, but the contents are transferred bit for bit into the corresponding second storage devices, (3) completely sequentially: the bits are transferred sequentially and successively for the various first storage devices into the corresponding bits of the second storage device (this is the longest variant timewise but also the one with the fewest parallel connections).

It is advantageous to read all detector modules simultaneously into a storage device inside a detector and which is a component of the peripheral electronic devices. Reading of all detector modules will hereinafter be called "reading". Data or image pre-processing can occur in the peripheral electronic devices, thus for example the compiling of the detector module readings to form an overall reading of all detector modules. In principle each reading could be depicted as an image. In general, however, a plurality of readings (i.e. for example all readings which occur during the X-ray window length) are compiled to form an image by adding all count signals. If a plurality of first and second storage units per pixel element are a component of the design, then a plurality of images (for example 4) result in accordance with the contents of the various storage units (for example FIG. 7).

In the case of continuous X-ray radiation, the X-ray window length matches the inverse image frequency since no dead times accrue due to the reading process.

The various readings (reading of the module contents of all detector modules) can be compiled to form an image. This can either be carried out in the X-ray detector or externally before actual image processing.

The advantages of the disclosed X-ray detector are inter alia as follows: significant degrees of design and application freedom result since the taking and reading processes are separated from each other in actuality. Continuous X-ray radiation may also be used (in particular for high-end 3D applications (flat-panel volume CT), without significant dead times (radiation without detection) occurring. The bit depths of the digital storage units (counters) can be optimized (i.e. reduced to the smallest possible size). The space requirement on each pixel element is consequently lower (one counting pixel element may require hundreds to well over 1,000 transistors depending on design). Smaller counter structures results in space on the pixel element for other functions.

Figure 9:
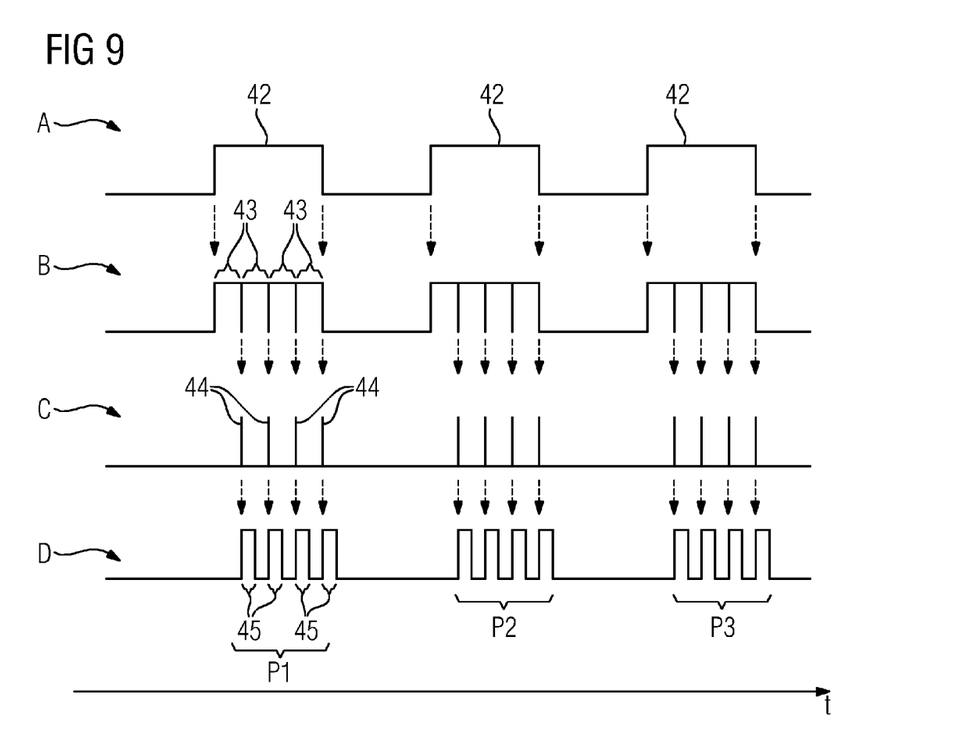
FIG. 9 shows a synchronous timing diagram of a method with pulsed X-ray radiation, according to one embodiment of the invention.
Figure 10:
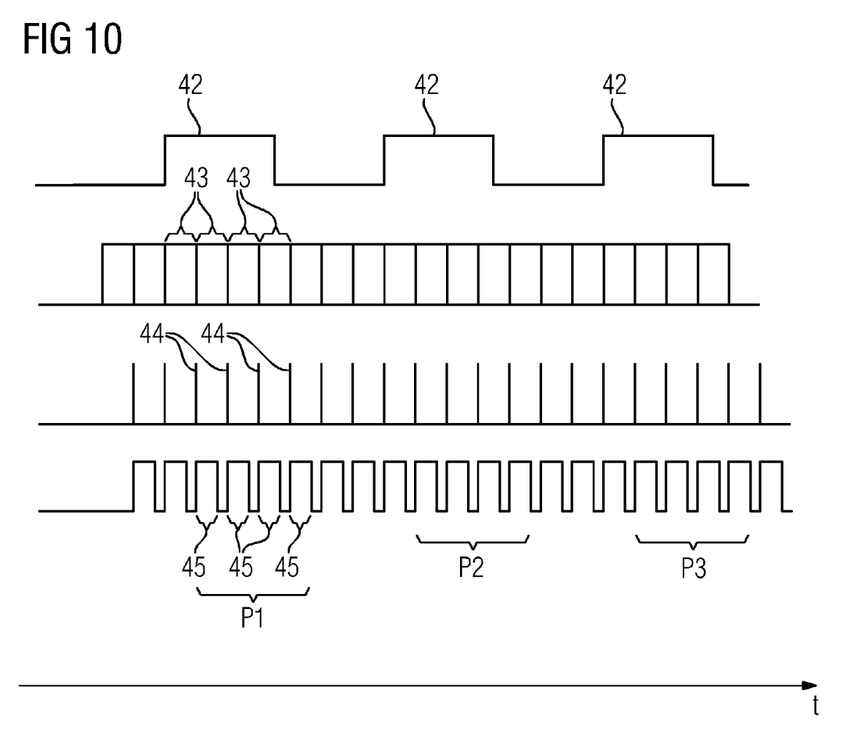
FIG. 10 shows an asynchronous timing diagram of a method with pulsed X-ray radiation, according to one embodiment of the invention.
Figure 11:
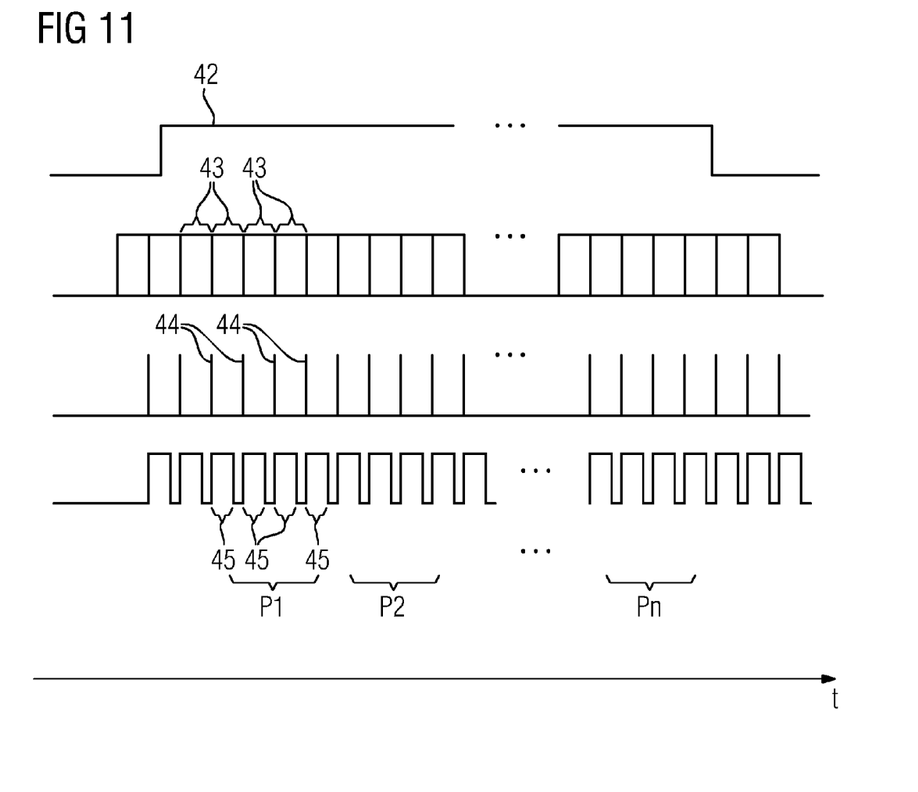
FIG. 11 shows an asynchronous timing diagram of a method with continuous X-ray radiation, according to one embodiment of the invention.

FIGS. 9 to 11 show some examples of a course over time of the method, wherein FIG. 9 shows synchronous counting and reading and FIGS. 10 and 11 show asynchronous counting and reading.

FIG. 9 shows synchronous control, wherein the start and end of the respective X-ray window (three X-ray windows 42 are shown) triggers the readings (four per X-ray pulse are shown here). As a result the allocation of the readings to the corresponding pulse and corresponding image is simple. The four counting intervals 43 per X-ray pulse during which count signals are respectively stored in the first storage units are shown under B). The instant of the transfer operation from the first storage units to the second storage units and the resetting of the first storage units is shown under C), wherein a very short transfer time 44 is assumed. The first storage units can be written on again directly thereafter. The module reading times 45 during which the second storage units are read are shown under D). Images are then compiled from various readings, for example from all readings of an X-ray pulse.

FIG. 10 shows asynchronous control. With asynchronous control between generator/X-ray tube and X-ray detector and pulsed X-ray radiation a plurality of readings with count content alternate with ones without count content (if the counting interval is small compared with pulse time and non-radiation time). Images pertaining to the corresponding pulses can then be generated in that averaged readings are added to an image until a reading without a count content appears. The next image is generated as soon as a reading with a count content appears again—corresponding to the next X-ray pulse.

FIG. 11 shows asynchronous control with continuous X-ray radiation. Here, depending on the desired image frequency, a certain number of readings can be defined which are allocated to one image.

Figure 12:
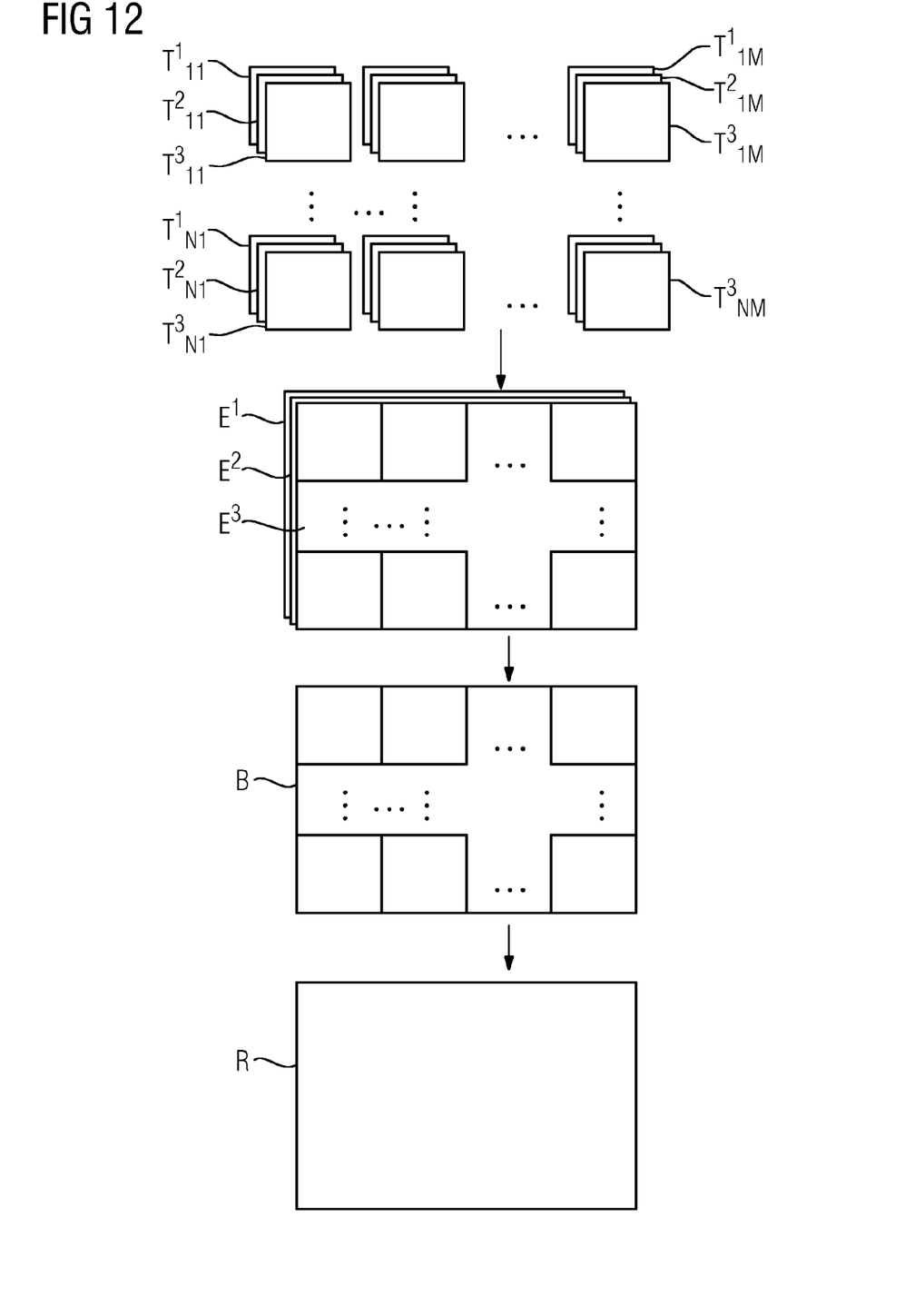
FIG. 12 shows a sequence of a method for compiling part images to form a corrected overall image.
Figure 13:
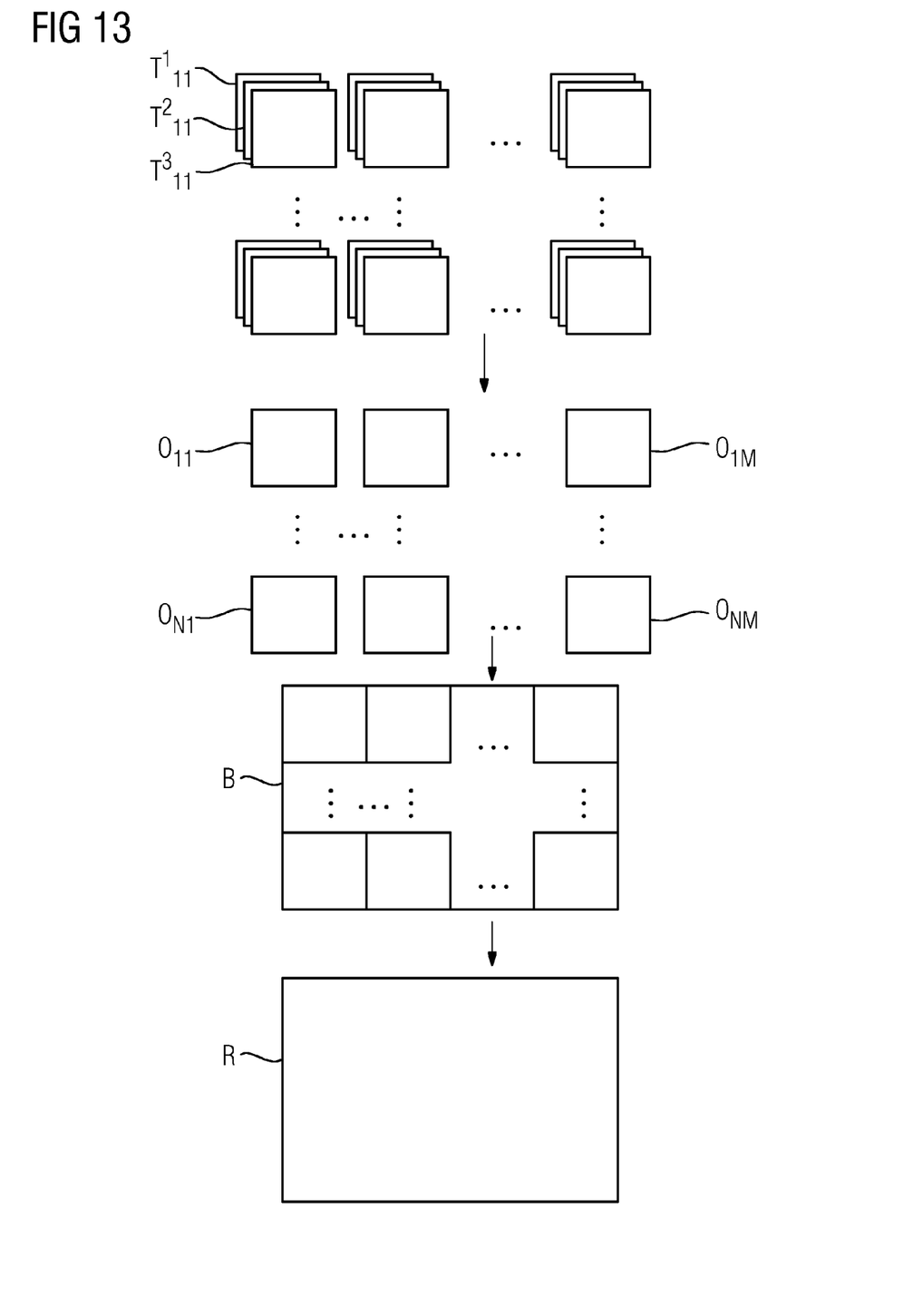
FIG. 13 shows a further sequence of a method for compiling part images to form a corrected overall image.

FIGS. 12 and 13 show two of several possibilities as to how an image can be compiled from the individual readings of a plurality of different detector modules to arrive at an artifact-free flat image. FIG. 12 shows how firstly for each reading x (in the case of three readings for example x=1 . . . 3) the image data of the part images $T_g^x$ of the individual detector modules are geometrically compiled at the positions ij (where i=1 . . . N and j=1 . . . M), so x reading images $E^x$ result. In the next step an average of all reading images $E^x$ is taken, so an overall image B results. Finally, corrections are carried out which deal for example with any artifacts at the module boundaries (for example a different geometry of the edge pixels form central pixels of the module) as well as further flat fielding corrections (defects, etc.) and the like, so a corrected overall image R is obtained. FIG. 13 shows how firstly the part images $T_g^x$ of the individual detector modules are averaged module-by-module at the positions ij (where i=1 . . . N and j=1 . . . M). The averaged module images $O_{ij}$ are then combined into an overall image B. Finally corrections are made which deal for example with any artifacts at the module boundaries, as well as further flat fielding corrections and the like, so a corrected overall image R is obtained. Other sequences are possible.

It is also possible to transfer aspects of the invention to indirectly converting X-ray detectors. The ASIC design is similar in this case but photodiodes are necessary. In addition, one or more optical coupling layer(s) are necessary between the indirect converter material (scintillator) and counting ASIC for example.

In addition to the use for interventional processes, in cardiology, radiology and surgery, aspects of the invention may also be used for other fields of application, such as radiography, mammography or computerized tomography.

Aspects of the invention may be summarized in brief as follows: to increase the frame rates and simultaneously improve the quality of X-ray images a counting digital X-ray detector for taking X-ray images of an object penetrated by X-ray radiation, having at least one detector module is provided, the detector module comprising a X-ray converter for converting X-ray radiation into an electrical signal and a matrix having a large number of counting pixel elements, wherein each counting pixel element has a signal input, a conversion device for converting the electrical signal into a count signal and a first digital storage unit for storing the count signal, wherein exactly one second digital storage unit is allocated to each first storage unit, and this is designed to form a copy of the first storage unit at the moment of transfer by way of a transfer process, and wherein the X-ray detector is designed such that the transfer process can be simultaneously carried out for the large number of pixel elements.

What is claimed is:

1. A counting digital X-ray detector for taking X-ray images of an object penetrated by X-ray radiation, comprising:
at least one detector module having:
an X-ray converter configured to convert X-ray radiation into an electrical signal, and
a matrix having a number of counting pixel elements, each counting pixel element comprising:
a signal input,
a conversion device configured to convert the electrical signal into a count signal,
a set of first digital storage units configured to store the count signal, and
a set of second digital storage units, wherein one second digital storage unit of the set of second storage units to each first storage unit and configured to form a copy of the information stored in the first storage unit at a moment of transfer by a transfer process, and
wherein the X-ray detector is configured such that the transfer process is executable simultaneously for all pixels of the number of counting pixel elements.

2. The X-ray detector of claim 1, wherein the conversion device includes a charge amplifier and at least one discriminator, each discriminator having an adjustable threshold value.

3. The X-ray detector of claim 2, wherein the conversion device includes a plurality of discriminators, each having different threshold values, and wherein the pixel element includes a plurality of first digital storage units for counting electrical signals of different energy levels.

4. The X-ray detector of claim 1, wherein the X-ray converter comprises a CdTe direct converter.

5. The X-ray detector of claim 1, wherein the X-ray detector has a number of detector modules.

6. The X-ray detector of claim 1, wherein each unit of the first set and the second set of digital storage units comprises a counter.

7. A method for taking a series of X-ray images of an object with a counting digital X-ray detector including at least one detector module having an X-ray converter and a matrix having a number of counting pixel elements, a conversion device, a set of first digital storage units, and a set of second digital storage units wherein one second digital storage unit of the set of second storage units to each first storage unit, the X-ray detector being configured such that a transfer process is executable simultaneously for all pixels of the number of counting pixel elements, the method comprising:
a) the conversion device of a particular detector module receiving X-ray radiation that has penetrated the object during an X-ray exposure and converting the received X-ray radiation into electrical signals in a spatially resolved manner,
b) the number of counting pixel elements converting the electrical signals, in a pixel-by-pixel manner, into count signals, and storing the count signals in respective first storage units,
c) simultaneously transferring the stored count signals of all pixel elements of the particular detector module from the respective first storage units into the associated second storage units and then resetting the first storage units to zero,
d) sequentially reading out the contents of the second storage units and resetting the second storage units to zero, and
e) repeating steps (a) to (d) multiple times, wherein steps (a) and (b) of a particular iteration occur at least partially during the occurrence of step (d) of the preceding iteration.

8. The method of claim 7, wherein the conversion device includes a charge amplifier and at least one discriminator, each discriminator having an adjustable threshold value.

9. The method of claim 8, wherein the conversion device includes a plurality of discriminators, each having different threshold values, and wherein the pixel element includes a plurality of first digital storage units for counting electrical signals of different energy levels.

10. The method of claim 7, wherein the X-ray converter comprises a CdTe direct converter.

11. The method of claim 7, wherein the X-ray detector has a number of detector modules.

12. The method of claim 7, wherein each unit of the first set and second set of digital storage units comprises a counter.

13. An X-ray system, comprising
an X-ray emitter configured to generate X-ray radiation toward an object; and
a counting digital X-ray detector for taking X-ray images of an object penetrated by X-ray radiation, the counting digital X-ray detector comprising:
at least one detector module having:
an X-ray converter configured to convert X-ray radiation into an electrical signal, and
a matrix having a number of counting pixel elements, each counting pixel element comprising:
a signal input,
a conversion device configured to convert the electrical signal into a count signal,
a set of first digital storage units configured to store the count signal, and
a set of second digital storage units wherein one second digital storage unit of the set of second storage units to each first storage unit and configured to form a copy of the information stored in the first storage unit at a moment of transfer by a transfer process, and
wherein the X-ray detector is configured such that the transfer process is executable simultaneously for all pixels of the number of counting pixel elements.

14. The X-ray system of claim 13, wherein the conversion device includes a charge amplifier and at least one discriminator, each discriminator having an adjustable threshold value.

15. The X-ray system of claim 14, wherein the conversion device includes a plurality of discriminators, each having different threshold values, and wherein the pixel element includes a plurality of first digital storage units for counting electrical signals of different energy levels.

16. The X-ray system of claim 13, wherein the X-ray converter comprises a CdTe direct converter.

17. The X-ray system of claim 13, wherein the X-ray detector has a number of detector modules.

18. The X-ray system of claim 13, wherein each unit of the first set and the second set of digital storage units comprises a counter.

* * * * *